United States Patent
Djalilian (10) Patent No.: US 12,220,389 B2
(45) Date of Patent: Feb. 11, 2025

(54) COMBINATION THERAPY FOR THE TREATMENT OF TINNITUS AND OTHER MEDICAL CONDITIONS

(71) Applicant: The Regents of the University of California, Oakland, CA (US)

(72) Inventor: Hamid Djalilian, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/210,046

(22) Filed: Jun. 14, 2023

(65) Prior Publication Data

US 2023/0321011 A1  Oct. 12, 2023

Related U.S. Application Data

(62) Division of application No. 16/686,057, filed on Nov. 15, 2019, now abandoned.

(60) Provisional application No. 62/768,820, filed on Nov. 16, 2018.

(51) Int. Cl.
| | |
|---|---|
| *A61K 31/137* | (2006.01) |
| *A61K 31/138* | (2006.01) |
| *A61K 31/195* | (2006.01) |
| *A61K 31/277* | (2006.01) |
| *A61K 31/357* | (2006.01) |
| *A61K 31/433* | (2006.01) |
| *A61K 31/4525* | (2006.01) |
| *A61P 27/16* | (2006.01) |

(52) U.S. Cl.
CPC .......... *A61K 31/137* (2013.01); *A61K 31/138* (2013.01); *A61K 31/195* (2013.01); *A61K 31/277* (2013.01); *A61K 31/357* (2013.01); *A61K 31/433* (2013.01); *A61K 31/4525* (2013.01); *A61P 27/16* (2018.01)

(58) Field of Classification Search
CPC ...... A61K 31/137; A61K 31/357; A61P 27/16
See application file for complete search history.

(56) References Cited

PUBLICATIONS

Sullivan et al. Arch Intern Med 1993, 153 (19), 2251-2259.*
Perez-Cisneros et al. Otolaryngology Head and Neck Surgery 2007, 132 (2-Suppl.), p. 245.*
Mikulec et al. American Journal of Otolaryngology—Head and Neck Medicine and Surgery 2012, 33, 121-127.*
Dobie, Ra. "A review of randomized clinical trials in tinnitus." Laryngoscope. 109(8):1202-11 (1999).
Duckert et al. "Treatment of tinnitus with intravenous lidocaine: a double-blind randomized trial." Otolaryngol Head Neck Surg. 91(5):550-5 (1983).
Evans et al., "Migraine with transient unilateral hearing loss and tinnitus." Headache 49(5):756-8 (2009).
Guichard et al., "Association Between Headaches and Tinnitus in Young Adults: Cross-Sectional Study." Headache. 56(6):987-94 (2016).
Hallam et al., "Tinnitus impairs cognitive efficiency." Int J Audiol. 43(4):218-26 (2004).
Landgrebe et al., "Structural brain changes in tinnitus: grey matter decrease in auditory and non-auditory brain areas." Neuroimage. 46(1):213-8 (2009).
Langguth et al., "Tinnitus and Headache." Biomed Res Int. 2015:797416 (2015).
Langguth et al., "Tinnitus Patients with Comorbid Headaches: The Influence of Headache Type and Laterality on Tinnitus Characteristics." Front Neurol. 8:440 (2017).
Lawther, Alex. Review of "Topiramate plus nortriptyline in the preventive treatment of migraine: a controlled study for nonresponders" by Krymchantowski et al. Document created Sep. 20, 2012. Available online at http://pharmacy.hsc.wvu.edu/media/1206/topiramate-plus-nortriptyline-for-migraine.pdf.
Llinas et al., "Thalamocortical dysrhythmia: A neurological and neuropsychiatric syndrome characterized by magnetoencephalography." Proc Natl Acad Sci U S A. 96(26):15222-7 (1999).
Minen et al., "The neuropsychiatry of tinnitus: a circuit-based approach to the causes and treatments available." J Neurol Neurosurg Psychiatry 85(10):1138-44 (2014).
Muhlau et al., "Structural brain changes in tinnitus." Cereb Cortex. 16(9):1283-8 (2006).
Muhlnickel et al. "Reorganization of auditory cortex in tinnitus." Proc Natl Acad Sci U S A. 95(17):10340-3 (1998).
Ploghaus et al., "Dissociating pain from its anticipation in the human brain." Science 284(5422):1979-81 (1999).
Price et al., "Neurocircuitry of mood disorders." Neuropsychopharmacology. 35(1):192-216 (2010).
Roberts et al., "Ringing ears: the neuroscience of tinnitus." J Neurosci. 30(45):14972-9. (2010).
Sindhusake et al., "Risk factors for tinnitus in a population of older adults: the blue mountains hearing study." Ear Hear. 24(6):501-7 (2003).
Wager et al., "Placebo-induced changes in FMRI in the anticipation and experience of pain." Science 303(5661):1162-7 (2004).

\* cited by examiner

*Primary Examiner* — Irina Neagu
(74) *Attorney, Agent, or Firm* — Gavrilovich, Dodd & Lindsey LLP (57) ABSTRACT

The disclosure provides for a combination therapy comprising different classes of medications for the treatment of tinnitus and other medical conditions, and methods of treatment thereof.

10 Claims, 1 Drawing Sheet

*FIG. 1*

| Study process Months | 1-2 | 3-4 | 5-6 | 7-8 | 9-10 | 11-12 |
|---|---|---|---|---|---|---|
| Study site coordination and team assignments | ▓ | | | | | |
| Subject recruitment and enrolment | ▓ | ▓ | | | | |
| Randomization and initiation of treatments | ▓ | ▓ | | | | |
| Patient follow up, outcome measurements, adverse event recording | | ▓ | ▓ | ▓ | ▓ | |
| Interval analysis of data | | | ▓ | | | |
| Completion of 6-month interim report | | | ▓ | | | |
| Final data analysis and assessment report | | | | | | ▓ |

*FIG. 2*

COMBINATION THERAPY FOR THE TREATMENT OF TINNITUS AND OTHER MEDICAL CONDITIONS

CROSS REFERENCE TO RELATED APPLICATIONS

This application is a Divisional application of prior U.S. application Ser. No. 16/686,057 filed Nov. 15, 2019 that claims priority under 35 U.S.C. § 119 from Provisional Application Ser. No. 62/768,820 filed Nov. 16, 2018, the disclosures of which are incorporated herein by reference

TECHNICAL FIELD

The disclosure provides for a combination therapy comprising different classes of medications for the treatment of tinnitus and other medical conditions, and methods of treatment thereof.

BACKGROUND

Tinnitus is the perception of sound in the absence of acoustic stimulation, and often involves sound sensations such as ringing, buzzing, roaring, whistling, and hissing that cannot be attributed to an external sound source. Tinnitus is a symptom associated with many forms of hearing loss and can also be a symptom of other health problems. It is estimated that more than 40 million people in the United States experience chronic tinnitus and 10 million of these people consider their tinnitus to be serious problem.

SUMMARY

There are presently no FDA-approved drugs specifically for tinnitus, and no medications that have been shown to reverse the neural hyperactivity at the root of tinnitus. The disclosure provides for combination therapies comprising different classes of medications that were shown to have efficacy based upon preliminary clinical data in a retrospective analysis of patients treated with the medications. More specifically it was found that a combination of medications from different drug classes provided beneficial or ameliorative effects in treating otologic conditions (e.g., tinnitus or vertigo) or an otologic symptom (e.g., tinnitus or vertigo) associated with a disease or disorder (e.g., headache or inflammatory intestinal disorder) in a subject in need thereof. For example, retrospective analysis of the preliminary clinical data indicated that an otologic condition or otologic symptom disclosed herein can be treated with a combined therapy of two or more drugs selected from the following drug classes: tricyclic antidepressants, anti-seizure medications, beta blockers, carbonic anhydrase inhibitors, selective serotonin reuptake inhibitors, selective norepinephrine reuptake inhibitors, calcium or sodium channel blockers, serotonin norepinephrine reuptake inhibitors, specific serotonin antidepressants, unicyclic antidepressants, tricyclic secondary amines, tricyclic tertiary amines, and antidepressants/serotonin modulators. In view of the improvements in primary and secondary treatment outcomes in the retrospective analysis, a large, randomized, double-blinded, placebo controlled, single institutional 12-week study is proposed herein.

In a particular embodiment, the disclosure provides for a composition for the treatment of an otologic condition, or an otologic symptom(s) associated with a disease or disorder, comprising therapeutically effective amounts of a first medication and a second medication selected from the following drug classes: tricyclic antidepressants, anti-seizure medications, beta blockers, carbonic anhydrase inhibitors, selective serotonin reuptake inhibitors, and calcium or sodium channel blockers, wherein the first medication is from a different drug class than the second medication. In a further embodiment, the ratio by weight of the first medication to the second medication in the composition is from 20:1 to 1:20. In yet a further embodiment of any of the foregoing embodiments, the ratio by weight of the first medication to the second medication in the composition is from 10:1 to 1:10. In yet a further embodiment of any of the foregoing embodiments, the first medication of the composition is a tricyclic antidepressant; and the second medication is selected from the group consisting of an anti-seizure medication, a beta blocker, a calcium or sodium channel blocker, and a carbonic anhydrase inhibitor. Examples of tricyclic antidepressants, include but are not limited to, amineptine, amitriptyline, amitriptylinoxide, amoxapine, butriptyline, clomipramine, demexiptiline, desipramine, dibenzepin, dimethacrine, dosulepine, doxepin, imipramine, imipraminoxide, iprindole, lofepramine, melitracen, metapramine, nitroxazepine, nortriptyline, noxiptyline, opipramol, pipofezine, propizepine, protriptyline, quinupramine, tianeptine, and trimipramine. In yet a further embodiment of any of the foregoing embodiments, the tricyclic antidepressant is nortriptyline or amitriptyline. In yet a further embodiment of any of the foregoing embodiments, the composition comprises nortriptyline at a dose of 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or 125 mg, or a range that includes or is between any two of the foregoing doses. In yet a further embodiment of any of the foregoing embodiments, the composition comprises amitriptyline at a dose of 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or 125 mg, or a range that includes or is between any two of the foregoing doses. In yet a further embodiment of any of the foregoing embodiments, the second medication is an anti-seizure medication selected from gabapentin and topiramate. In yet a further embodiment of any of the foregoing embodiments, the second medication is propranolol, a beta blocker. In yet a further embodiment of any of the foregoing embodiments, the second medication verapamil, a calcium or sodium channel blocker. In yet a further embodiment of any of the foregoing embodiments, the second medication is acetazolamide, a carbonic anhydrase inhibitor. In yet a further embodiment of any of the foregoing embodiments, the first medication of the composition is a selective serotonin inhibitor; and the second medication of the composition is selected from the group consisting of an anti-seizure medication, a beta blocker, a sodium or calcium channel blocker, and a carbonic anhydrase inhibitor. In yet a further embodiment of any of the foregoing embodiments, the first medication is a selective serotonin inhibitor selected from the group consisting of citalopram, escitalopram, fluoxetine, fluvoxamine, indalpine, paroxetine, sertraline, and zimelidine. In yet a further embodiment of any of the foregoing embodiments, the first medication is paroxetine. In yet a further embodiment of any of the foregoing embodiments, the composition comprises paroxetine at a dose of 3 mg, 5 mg, 10 mg, 12 mg, 14 mg, 15 mg, 16 mg, 18 mg, 20 mg, 22 mg, 24 mg, 25 mg, 26 mg, 28 mg, 30 mg, 32 mg, 34 mg, 35 mg, 36 mg, 38 mg, 40 mg, or a range that includes or is between any two of the foregoing doses. In yet a further embodiment of any of the foregoing embodiments, the second medication is an anti-seizure medication selected from gabapentin and topiramate. In yet a further embodiment of any of the foregoing embodiments, the second medication is propranolol, a beta blocker. In yet a further embodiment of any of the foregoing embodiments, the second medication is verapamil, a calcium or sodium channel blocker. In yet a further embodiment of any of the foregoing embodiments, the second medication is acetazolamide, a carbonic anhydrase inhibitor. In yet a further embodiment of any of the foregoing embodiments, the first medication is a calcium or sodium channel blocker; and the second medication is selected from the group consisting of a tricyclic antidepressant, an anti-seizure medication, and a carbonic anhydrase inhibitor. In yet a further embodiment of any of the foregoing embodiments, the calcium or sodium channel blocker is selected from the group consisting of ethadione, paramethadione, trimethadione, ethosuximide, mesuximide, phensuximide, gabapentin, pregabalin, imepitoin, lamotrigine, topiramate, verapamil, and zonisamide. In yet a further embodiment of any of the foregoing embodiments, the first medication is verapamil. In yet a further embodiment of any of the foregoing embodiments, the composition comprises verapamil at a dose of 20 mg, 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, or a range that includes or is between any two of the foregoing doses. In yet a further embodiment of any of the foregoing embodiments, the second medication is a tricyclic antidepressant selected from nortriptyline and amitriptyline. In yet a further embodiment of any of the foregoing embodiments, the second medication is an antiseizure medication selected from gabapentin and topiramate. In yet a further embodiment of any of the foregoing embodiments, the second medication is acetazolamide, a carbonic anhydrase inhibitor. In yet a further embodiment of any of the foregoing embodiments, the first medication of the composition is an anti-seizure medication; and the second medication of the composition is selected from the group consisting of a tricyclic antidepressant, a selective serotonin inhibitor, a beta blocker, and a sodium or calcium channel blocker. In yet a further embodiment of any of the foregoing embodiments, the anti-seizure medication is selected from the group consisting of acetazolamide, carbamazepine, clobazam, clonazepam, diazepam, divalproex sodium, ethosuximide, ethotoin, felbamate, fosphenytoin, gabapentin, lamotrigine, lacosamide, levetiracetam, lorazepam, mephenyloin, metharbital, methsuximide, methazolamide, nitrazepam, oxcarbazepine, phenobarbital, phenytoin, phensuximide, pregabalin, primidone, rufinamide, sodium valproate, stiripentol, tiagabine, topiramate, trimethadione, valproic acid, vigabatrin, and zonisamide. In yet a further embodiment of any of the foregoing embodiments, the first medication is gabapentin or topiramate. In yet a further embodiment of any of the foregoing embodiments, the composition comprises gabapentin at a dose of 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, or a range that includes or is between any two of the foregoing doses. In yet a further embodiment of any of the foregoing embodiments, the composition comprises topiramate at a dose of 7 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, or a range that includes or is between any two of the foregoing doses. In yet a further embodiment of any of the foregoing embodiments, the first medication of the composition is a carbonic anhydrase inhibitor; and the second medication of the composition is selected from the group consisting of a tricyclic antidepressant, a selective serotonin inhibitor, a and a sodium or calcium channel blocker. In yet a further embodiment of any of the foregoing embodiments, the carbonic anhydrase inhibitor is selected from acetazolamide, dichlorphenamide, and zonisamide. In yet a further embodiment of any of the foregoing embodiments, the carbonic anhydrase inhibitor is acetazolamide. In yet a further embodiment of any of the foregoing embodiments, the composition comprises acetazolamide at a dose of 60 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, or a range that includes or is between any two of the foregoing doses. In yet a further embodiment of any of the foregoing embodiments, the first medication of the composition is a beta blocker; and the second medication of the composition is selected from a tricyclic antidepressant and a selective serotonin reuptake inhibitor. In yet a further embodiment of any of the foregoing embodiments, the beta blocker is selected from the group consisting of alprenolol, bopindolol, bupranolol, carteolol, cloranolol, mepindolol, nadolol, oxprenolol, penbutolol, pindolol, iodopindolol, propranolol, sotalol, tertatolol, timolol, acebutolol, atenolol, betaxolol, bevantolol, bisoprolol, celiprolol, epanolol, esmolol, landiolol, metoprolol, nebivolol, practolol, S-atenolol, talinolol, butaxamine, arotinolol, carvedilol, and labetalol. In yet a further embodiment of any of the foregoing embodiments, the beta blocker is propranolol. In yet a further embodiment of any of the foregoing embodiments, the composition comprises propranolol at a dose of 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg or a range that includes or is between any two of the foregoing doses. In yet a further embodiment of any of the foregoing embodiments, the composition is a pharmaceutically acceptable composition that further comprises excipient(s), diluent(s) and/or carrier(s). In yet a further embodiment of any of the foregoing embodiments, the composition is formulated for oral delivery. In yet a further embodiment of any of the foregoing embodiments, the composition is in the form of a pill, tablet, or capsule. In yet a further embodiment of any of the foregoing embodiments, the composition is formulated as a single unit dose. In yet a further embodiment of any of the foregoing embodiments, the composition is formulated as a multi-unit dose. In yet a further embodiment of any of the foregoing embodiments, the composition comprises a submaximal dose of the first medication and/or a submaximal dose of the second medication. In yet a further embodiment of any of the foregoing embodiments, the composition comprises less than about 75%, 60%, 50%, 40%, 30%, 20%, or 10% of the maximal dose of the first medication and/or the second medication.

In a certain embodiment, the disclosure also provides a method of treating an otologic condition, or an otologic symptom(s) associated with a disease or disorder, in a subject in need thereof, comprising: administering to the subject a combined therapy comprising therapeutically effective amounts of two or more medications selected from the following drug classes: tricyclic antidepressants, anti-seizure medications, beta blockers, carbonic anhydrase inhibitors, selective serotonin reuptake inhibitors, and calcium or sodium channel blockers, wherein the two or more medications are from different drug classes. In a further embodiment, the otologic condition is selected from the group consisting of tinnitus, fluctuating or sudden hearing loss, sensorineural hearing loss, dizziness, vertigo, aural pressure/pain, and fluctuating hearing loss. In yet a further embodiment of any of the foregoing embodiments, the otologic symptom(s) associated with a disease or disorder comprises tinnitus and/or vertigo. In yet a further embodiment of any of the foregoing embodiments, the otologic symptom(s) are associated with a disease or disorder selected from the group consisting of neck pain, headache, irritable bowel syndrome, interstitial cystitis, migraine-related disorders, and fibromyalgia. In yet a further embodiment of any of the foregoing embodiments, the subject is a human patient having the otologic symptom(s) of tinnitus and/or vertigo. In yet a further embodiment of any of the foregoing embodiments, one of the medications of the combined therapy is a tricyclic antidepressant selected from the group consisting of amineptine, amitriptyline, amitriptylinoxide butriptyline, clomipramine, demexiptiline, desipramine, dibenzepin, dimethacrine, dosulepine, doxepin, imipramine, imipraminoxide, iprindole, lofepramine, melitracen, metapramine, nitroxazepine, nortriptyline, noxiptyline, opipramol, pipofezine, propizepine, protriptyline, quinupramine, tianeptine, and trimipramine. In yet a further embodiment of any of the foregoing embodiments, the tricyclic antidepressant is nortriptyline or amitriptyline. In yet a further embodiment of any of the foregoing embodiments, nortriptyline is administered at a dose of 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or 125 mg, or a range that includes or is between any two of the foregoing doses. In yet a further embodiment of any of the foregoing embodiments, amitriptyline is administered at a dose of 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or 125 mg, or a range that includes or is between any two of the foregoing doses. In yet a further embodiment of any of the foregoing embodiments, one of the medications of the combined therapy is an anti-seizure medication selected from the group consisting of acetazolamide, carbamazepine, clobazam, clonazepam, diazepam, divalproex sodium, ethosuximide, ethotoin, felbamate, fosphenytoin, gabapentin, topiramate, lamotrigine, lacosamide, levetiracetam, lorazepam, mephenyloin, metharbital, methsuximide, methazolamide, nitrazepam, oxcarbazepine, phenobarbital, phenytoin, phensuximide, pregabalin, primidone, rufinamide, sodium valproate, stiripentol, tiagabine, trimethadione, valproic acid, vigabatrin, and zonisamide. In yet a further embodiment of any of the foregoing embodiments, the anti-seizure medication is topiramate or gabapentin. In yet a further embodiment of any of the foregoing embodiments, topiramate is administered at a dose of 7 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, or a range that includes or is between any two of the foregoing doses. In yet a further embodiment of any of the foregoing embodiments, gabapentin is administered at a dose of 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, or a range that includes or is between any two of the foregoing doses. In yet a further embodiment of any of the foregoing embodiments, one of the medications of the combined therapy is a beta blocker selected from the group consisting of alprenolol, bopindolol, bupranolol, carteolol, cloranolol, mepindolol, nadolol, oxprenolol, penbutolol, pindolol, iodopindolol, propranolol, sotalol, tertatolol, timolol, acebutolol, atenolol, betaxolol, bevantolol, bisoprolol, celiprolol, epanolol, esmolol, landiolol, metoprolol, nebivolol, practolol, S-atenolol, talinolol, butaxamine, arotinolol, carvedilol, and labetalol. In yet a further embodiment of any of the foregoing embodiments, the beta blocker is propranolol. In yet a further embodiment of any of the foregoing embodiments, propranolol is administered at a dose of 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg or a range that includes or is between any two of the foregoing doses. In yet a further embodiment of any of the foregoing embodiments, one of the medications of the combined therapy is a carbonic anhydrase inhibitor selected from the group consisting of acetazolamide, dichlorphenamide, and zonisamide. In yet a further embodiment of any of the foregoing embodiments, the carbonic anhydrase inhibitor is acetazolamide. In yet a further embodiment of any of the foregoing embodiments, acetazolamide is administered at a dose of 60 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, or a range that includes or is between any two of the foregoing doses. In yet a further embodiment of any of the foregoing embodiments, one of the medications of the combined therapy is a selective serotonin reuptake inhibitor selected from the group consisting of citalopram, escitalopram, fluoxetine, fluvoxamine, indalpine, paroxetine, sertraline, and zimelidine. In yet a further embodiment of any of the foregoing embodiments, the selective serotonin reuptake inhibitor is paroxetine. In yet a further embodiment of any of the foregoing embodiments, paroxetine is administered at a dose of 3 mg, 5 mg, 10 mg, 12 mg, 14 mg, 15 mg, 16 mg, 18 mg, 20 mg, 22 mg, 24 mg, 25 mg, 26 mg, 28 mg, 30 mg, 32 mg, 34 mg, 35 mg, 36 mg, 38 mg, 40 mg, or a range that includes or is between any two of the foregoing doses. In yet a further embodiment of any of the foregoing embodiments, one of the medications of the combined therapy is a calcium or sodium channel blocker selected from the group consisting of ethadione, paramethadione, trimethadione, ethosuximide, mesuximide, phensuximide, gabapentin, pregabalin, imepitoin, lamotrigine, verapamil, and zonisamide. In yet a further embodiment of any of the foregoing embodiments, the calcium or sodium channel blocker is verapamil. In yet a further embodiment of any of the foregoing embodiments, verapamil is administered at a dose of 20 mg, 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, or a range that includes or is between any two of the foregoing doses. In yet a further embodiment of any of the foregoing embodiments, the combined therapy comprises nortriptyline and topiramate; nortriptyline and gabapentin; amitriptyline and topiramate; amitriptyline and gabapentin; nortriptyline and propranolol; amitriptyline and propranolol; nortriptyline and verapamil; amitriptyline and verapamil; nortriptyline and acetazolamide; amitriptyline and acetazolamide; paroxetine and topiramate; paroxetine and gabapentin; paroxetine and propranolol; paroxetine and verapamil; paroxetine and acetazolamide; verapamil and topiramate; verapamil and gabapentin; or verapamil and acetazolamide. In yet a further embodiment of any of the foregoing embodiments, the medications of the combined therapy are concomitantly administered. In yet a further embodiment of any of the foregoing embodiments, the medications of the combined therapy are sequentially administered. In yet a further embodiment of any of the foregoing embodiments, the medications of the combined therapy are administered at submaximal doses. In yet a further embodiment of any of the foregoing embodiments, each medication of the combined therapy is administered at 75%, 60%, 50%, 40%, 30%, 20%, or 10% of the maximal dose for the medication. In yet a further embodiment of any of the foregoing embodiments, the combined therapy is prepared as pharmaceutical composition(s) formulated for oral administration. In yet a further embodiment of any of the foregoing embodiments, the medications of the combined therapy are formulated as a single unit oral dosage form for oral administration. In yet a further embodiment of any of the foregoing embodiments, the medications of the combined therapy are formulated as multi-unit oral dosage forms for oral administration. In yet a further embodiment of any of the foregoing embodiments, the subject has tinnitus, and the administration of the combined therapy to the subject provides one or more of the following effects: improvement in a subject's tinnitus functional index; a decrease in the average number days in which the subject has annoying tinnitus; and/or a decrease in the level of tinnitus loudness.

In a particular embodiment, the disclosure further provides a composition for the treatment of an otologic condition, or an otologic symptom(s) associated with a disease or disorder, comprising therapeutically effective amounts of a first medication and a second medication selected from the following drug classes: tricyclic antidepressants, anti-seizure medications, beta blockers, carbonic anhydrase inhibitors, selective serotonin reuptake inhibitors, and calcium or sodium channel blockers, wherein the first medication is from a different drug class than the second medication. In a further embodiment, the first medication of the composition is a tricyclic antidepressant; and the second medication is selected from the group consisting of an anti-seizure medication, a beta blocker, a calcium or sodium channel blocker, and a carbonic anhydrase inhibitor. In yet a further embodiment of any of the foregoing embodiments, the first medication of the composition is a selective serotonin inhibitor; and the second medication of the composition is selected from the group consisting of an anti-seizure medication, a beta blocker, a sodium or calcium channel blocker, and a carbonic anhydrase inhibitor. In yet a further embodiment of any of the foregoing embodiments, the first medication is a calcium or sodium channel blocker; and the second medication is selected from the group consisting of a tricyclic antidepressant, an anti-seizure medication, and a carbonic anhydrase inhibitor. In yet a further embodiment of any of the foregoing embodiments, the first medication of the composition is an anti-seizure medication; and the second medication of the composition is selected from the group consisting of a tricyclic antidepressant, a selective serotonin inhibitor, a beta blocker, and a sodium or calcium channel blocker. In yet a further embodiment of any of the foregoing embodiments, the first medication of the composition is a carbonic anhydrase inhibitor; and the second medication of the composition is selected from the group consisting of a tricyclic antidepressant, a selective serotonin inhibitor, a and a sodium or calcium channel blocker. In yet a further embodiment of any of the foregoing embodiments, the first medication of the composition is a beta blocker; and the second medication of the composition is selected from a tricyclic antidepressant and a selective serotonin reuptake inhibitor. In yet a further embodiment of any of the foregoing embodiments, the first medication and the second medication combinations are selected from the group consisting of nortriptyline and topiramate, nortriptyline and gabapentin, amitriptyline and topiramate, amitriptyline and gabapentin, nortriptyline and propranolol, amitriptyline and propranolol, nortriptyline and verapamil, amitriptyline and verapamil, nortriptyline and acetazolamide, amitriptyline and acetazolamide, paroxetine and topiramate, paroxetine and gabapentin, paroxetine and propranolol, paroxetine and verapamil, paroxetine and acetazolamide, verapamil and topiramate, verapamil and gabapentin, and verapamil and acetazolamide. In yet a further embodiment of any of the foregoing embodiments, the composition is formulated for oral delivery and is in the form of a pill, a tablet, or a capsule. In yet a further embodiment of any of the foregoing embodiments, the composition comprises less than about 75% of the maximal dose of the first medication and/or the second medication.

In a certain embodiment, the disclosure provides a method of treating an otologic condition, or an otologic symptom(s) associated with a disease or disorder, in a subject in need thereof, comprising: administering to the subject a combined therapy comprising therapeutically effective amounts of two or more medications selected from the following drug classes: tricyclic antidepressants, anti-seizure medications, beta blockers, carbonic anhydrase inhibitors, selective serotonin reuptake inhibitors, and calcium or sodium channel blockers, wherein the two or more medications are from different drug classes. In a further embodiment, the otologic condition is selected from the group consisting of tinnitus, fluctuating or sudden hearing loss, sensorineural hearing loss, dizziness, vertigo, aural pressure/pain, and fluctuating hearing loss, and wherein the otologic symptom(s) associated with a disease or disorder comprises tinnitus and/or vertigo. In yet a further embodiment of any of the foregoing embodiments, the subject is a human patient having tinnitus. In yet a further embodiment of any of the foregoing embodiments, administration of the combined therapy to the subject provides one or more of the following effects: improvement in a subject's tinnitus functional index; a decrease in the average number days in which the subject has annoying tinnitus; and/or a decrease in the level of tinnitus loudness. In yet a further embodiment of any of the foregoing embodiments, combinations of the two or more medications of the combined therapy are selected from the group consisting of: a tricyclic antidepressant and an anti-seizure medication, a tricyclic antidepressant and a beta blocker, a tricyclic antidepressant and a sodium or calcium channel blocker, a tricyclic antidepressant and a carbonic anhydrase inhibitor, a selective serotonin reuptake inhibitor and anti-seizure medication, a selective serotonin reuptake inhibitor and a beta blocker, a selective serotonin inhibitor and a sodium or calcium channel blocker, an anti-seizure medication and a sodium or calcium channel blocker, and a sodium or calcium channel blocker and a carbonic anhydrase inhibitor. In yet a further embodiment of any of the foregoing embodiments, the two or more medications of the combined therapy are selected from the group consisting of: nortriptyline, topiramate, amitriptyline, gabapentin, propranolol, verapamil, acetazolamide, and paroxetine. In yet a further embodiment of any of the foregoing embodiments, combinations of the two or more medications of the combined therapy are selected from the group consisting of: nortriptyline and topiramate, nortriptyline and gabapentin, amitriptyline and topiramate, amitriptyline and gabapentin, nortriptyline and propranolol, amitriptyline and propranolol, nortriptyline and verapamil, amitriptyline and verapamil, nortriptyline and acetazolamide, amitriptyline and acetazolamide, paroxetine and topiramate, paroxetine and gabapentin, paroxetine and propranolol, paroxetine and verapamil, paroxetine and acetazolamide, verapamil and topiramate, verapamil and gabapentin, and verapamil and acetazolamide. In yet a further embodiment of any of the foregoing embodiments, the two or more medications of the combined therapy are concomitantly administered. In yet a further embodiment of any of the foregoing embodiments, the two or more medications of the combined therapy are sequentially administered. In yet a further embodiment of any of the foregoing embodiments, the two or more medications of the combined therapy is administered at less than about 75% of the maximal dose for the two or more medications.

DETAILED DESCRIPTION

As used herein and in the appended claims, the singular forms "a," "an," and "the" include plural referents unless the context clearly dictates otherwise. Thus, for example, reference to "a bleb" includes a plurality of such vesicles and reference to "the extracellular vesicle" includes reference to one or more extracellular vesicles and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

It should be understood that this invention is not limited to the particular methodology, protocols, and reagents, etc., described herein and as such may vary. The terminology used herein is for the purpose of describing particular embodiments only and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%.

The term "co-administration", "in combination with", "a combination of" or "administered along with" may be used interchangeably and, as used herein, refers to two or more medical agents (e.g., drugs) being found in the patient's bloodstream at the same time, regardless of when or how they are actually administered. In one embodiment, the agents are administered simultaneously. In another embodiment, administration in combination is accomplished by combining the agents in a single dosage form. In yet another embodiment, the agents are administered sequentially. In a further embodiment the agents are administered through the same route. For example, in some embodiments, both agents are administered orally. In yet a further embodiment, the agents are administered through different routes. For example, in one embodiment, one agent is administered orally and the other agent is administered parenterally.

The terms "patient", "subject" and "individual" are used interchangeably herein, and refer to an animal, particularly a human, to whom treatment including prophylaxis treatment is provided. This includes human and non-human animals. The term "non-human animals" and "non-human mammals" are used interchangeably herein includes all vertebrates, e.g., mammals, such as non-human primates, (particularly higher primates), sheep, dog, rodent (e.g., mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. "Mammal" refers to any animal classified as a mammal, including humans, non-human primates, domestic and farm animals, and zoo, sports, or pet animals, such as dogs, cats, cattle, horses, sheep, pigs, goats, rabbits, etc. Patient or subject includes any subset of the foregoing, e.g., all of the above, but excluding one or more groups or species such as humans, primates or rodents. A subject can be male or female. A subject can be a fully developed subject (e.g., an adult) or a subject undergoing the developmental process (e.g., a child, infant or fetus).

The term "pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

The term "therapeutically effective amount" as used herein, refers to an amount that is sufficient to affect a therapeutically significant reduction in one or more symptoms of the condition when administered to a typical subject who has the condition. A therapeutically significant reduction in a symptom is, e.g., about 10%, about 20%, about 30%, about 40%, about 50%, about 60%, about 70%, about 80%, about 90%, about 100%, or more as compared to a control or non-treated subject.

The term "treat" or "treatment" as used herein, refers to a therapeutic treatment wherein the object is to eliminate or lessen a condition or a symptom. Beneficial or desired clinical results include, but are not limited to, elimination of symptoms or a condition, alleviation of symptoms or a condition, diminishment of extent of the condition or symptom, stabilization (i.e., not worsening) of the state of the condition or symptom, and delay or slowing of progression of the condition or symptoms. In a particular embodiment, treatment of a subject with a combined medical therapy disclosed herein results in improvement in a subject's tinnitus functional index; a decrease in the average number days in which the subject has annoying tinnitus; a decrease in the level of tinnitus loudness; and/or improvement in aural pressure/pain, fluctuating hearing loss, dizziness/vertigo, neck stiffness/headache, irritable bowel syndrome/interstitial cystitis, and/or fibromyalgia.

Tinnitus is defined as a perception of sound in the absence of external stimuli. Tinnitus is characterized by an auditory sensation in the absence of external sound. In many cases tinnitus is subjectively perceptual, i.e., only the subject can perceive symptoms. Symptoms of tinnitus include ringing, roaring, static, buzzing, hissing and whistling in one or both ears. The noise may be intermittent or continuous. In a nationwide study in the United States, about 50 million individuals (aged 20 years or older) reported having tinnitus in the preceding 12 months, with 16 million reporting tinnitus to occur at least once a day. In a cross-sectional analysis of U.S. representative demographic and audiometric data, it was shown that approximately 2.5 million individuals aged 12 to 19 years in the United States have experienced at least one episode of tinnitus, and this condition is chronic in about 1.6 million individuals in the same age category. If left untreated, tinnitus may lead to mental and psychological problems, such as depression, anxiety, panic, and cognitive defects, especially in older patients. It also represents one of the most common and distressing problems in otology practice, and it causes various somatic and psychological disorders that interfere with the quality of life. Despite many studies designed to find the mechanisms causing tinnitus, its pathophysiology remains poorly understood. In spite of the large economic and emotional impact of tinnitus, currently there is no FDA-approved medication to treat this debilitating condition.

Current treatments for tinnitus can be categorized into dietary and lifestyle modifications, medical treatments, cognitive behavioral therapy, and sound therapy. However, there is no FDA-approved medicine for treatment of tinnitus. The medications most often used in tinnitus management are psychoactive drugs that treat psychological issues arising from tinnitus. These drugs can help relieve the stress, anxiety, and depression related to tinnitus, minimizing the psychological burden of the condition. Because there is a circular relationship between negative emotions and tinnitus (tinnitus causes anxiety, which makes tinnitus seem worse, which causes more anxiety, etc.), it is also possible that psychoactive drugs may make tinnitus itself less noticeable for some patients. *The Cochrane Library* reveals six clinical trials (including 610 patients) evaluated the effectiveness of antidepressants in treatment of tinnitus. However, the trials' quality was generally low and none of them met the highest quality standard due to use of inadequate outcome measures and large drop-out rates. Hence, they concluded there is as yet insufficient evidence to say that antidepressant drug therapy improves tinnitus and further research is required.

The last decade saw an uptick in reports possibly implicating that there is a relationship between tinnitus and migraine. Such findings, however, were in direct contrast with the previously held and popular notion that migraine will seldom have a negative impact on the auditory pathways and generate cochlear symptoms, such as hearing loss or tinnitus. Recent studies showed that between 26-47% of patients with tinnitus suffer from concomitant headache, which was further supported by a large-scale cohort study.

A growing number of neuroimaging studies have been published in recent years consistently describing pathophysiological changes in brain regions beyond the auditory system, specifically in limbic structures. When analyzing these structural and functional changes associated with tinnitus, one can appreciate the anatomical overlap with the fronto-subcortical loop circuits affected in mood and anxiety disorders. The mechanism by which these changes are facilitated in tinnitus remains unknown, although various hypotheses have been proposed in the art. Although the pathophysiology of tinnitus and mood, anxiety or pain disorders will certainly be different, the functional neuroanatomy and some basic physiological principles (i.e., maladaptive plasticity) may not be that different. The study showed that the cumulative incidence of cochlear symptoms, defined as tinnitus, hearing loss, and/or sudden deafness was significantly higher in patients with history of migraine headaches than those without a migraine history.

Figure 1:
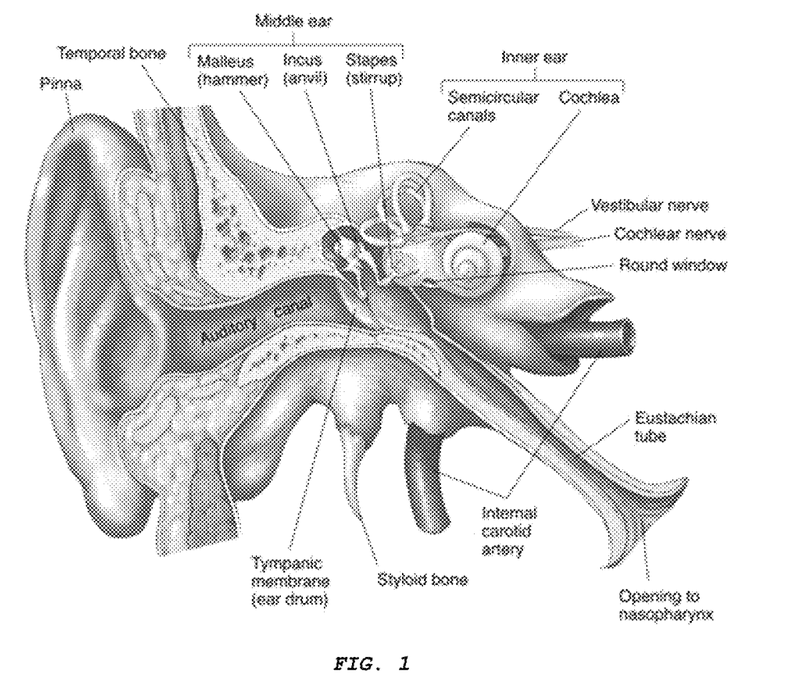
FIG. 1 provides a diagram of the anatomy of a human ear.
Figure 2:
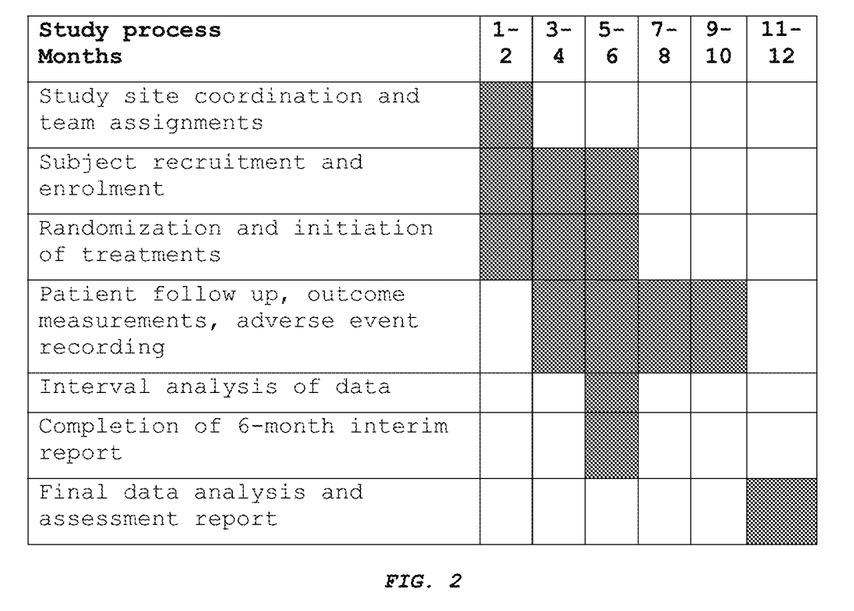
FIG. 2 provides an embodiment of a 12-month course (timeline table) to investigate the combined therapy disclosed herein in a large, randomized, double-blinded, and placebo-controlled study.

It is postulated herein that migraine-related cochlear (i.e., tinnitus, hearing loss) and vestibular (balance) symptoms can result from compromised blood flow to the inner ear (see FIG. 1) and to the brain as a result of vasospasm of the branches of the posterior cerebral circulation as well as possibly trigeminal neurogenic inflammation. It was postulated herein, that even patients without depression or other neuropsychiatric symptoms would benefit from receiving antidepressant drugs, such as nortriptyline and amitriptyline, due to a similar or common pathophysiological basis. In other words, one of the possible explanations for association of pain (i.e., headache) and tinnitus is thalamocortical dysrhythmia. In this proposed model, development of γ band activity related to the tinnitus percept serves as the pathophysiological model linking these two conditions. Tinnitus (similarly to chronic pain) may further have a peripheral physiological origin, but then the stimulus becomes established in the brain. For example, a correlation between the subjective strength of stimulus and the amount of cortical reorganization, is in line with studies looking at phantom limb pain in upper extremity amputees.

Based upon the foregoing analysis, an innovative approach was developed herein for the treatment of tinnitus that utilizes novel combinations of medications as well as other treatment options. In a further embodiment, the disclosure further provides for a step-wise combined treatment regimen comprising of an algorithm of escalating doses of a first medication (e.g., nortriptyline (antidepressant)) to a second medication (e.g., topiramate (anti-seizure medication)). The escalation of the doses can be based on patient symptoms and the severity thereof. For example, if the first medication is nortriptyline, nortriptyline can be titrated from 7.5 mg up to 60 mg in 7.5 mg steps. Similarly, if the second mediation is topiramate, topiramate can be titrated from 10 mg up to 80 mg in 10 mg steps every week concurrently with step-wise adjustment of the first medication, like nortriptyline. Given the risk of intolerance or possible side effects with migraine medications, patients are often started on a low dose with gradual escalation if their symptoms are not controlled. Based upon empiric and clinical experiences, it is believed that the combined therapy disclosed herein is efficacious with a small negative side-effect profile. For instance, in previous studies on Meniere's disease (in which tinnitus is one of the main symptoms), it was found that tinnitus-related quality of life scores increased (improved quality of life) from 0.91±1.08 pre-treatment to 1.26±1.32 post-treatment ($p<0.001$) with a combined therapy treatment.

In view positive results of pilot studies demonstrating efficacy of the combined treatment regimens disclosed herein, a randomized double-blinded placebo-controlled large-scale studies are currently being considered for tinnitus and other conditions, including dizziness, fluctuating or sudden hearing loss, sensorineural hearing loss, and dizziness. Further, it is expected that the large studies would utilize a step-wise regimen as described above. The subjects will be randomly assigned to experimental and control groups. The experimental group will receive combined treatment regimen (e.g., use of nortriptyline with topiramate) and the control group will receive a placebo daily. Both groups will be followed up over a course of 8 weeks. Primary treatment outcomes will be evaluated, and potential adverse events will be recorded for safety analysis. Secondary treatment outcomes will also be evaluated. Preliminary clinical data in a retrospective analysis of patients treated with the proposed medications have shown improvement in primary and secondary treatment outcomes, suggesting potential effectiveness of these treatments.

Further follow-on studies will look at the most effective dosage of the combined therapy. In such studies, subjects in the experimental group will start the study using an initial low dosage of the first and second medications. Such a dosage may be administered concurrently (e.g., use of single dosage form that comprises both medications) or sequentially (e.g., use of separate dosage forms administered at different time points). On a weekly basis, the subjects will be instructed to increase the dosage of the first and second medications if their symptoms do not improve. This process will continue until a maximum safe dosage is reached. Subjects will further be instructed to avoid increasing their medication dosage if their symptoms are under control. Subjects in the control group will also be asked to increase the dosage of placebo dosage form(s) (provided to be similar to the dosage forms used in the experimental group) every week if they do not experience improvement in symptoms. Those reporting side effects will be seen and examined to assess the safety of their continued enrollment and/or need for additional treatment.

The disclosure provides for a combined therapy that was shown to have efficacy based upon preliminary clinical data in a retrospective analysis of patients treated with the medications which showed improvement in primary and secondary treatment outcomes. More specifically it was found that a combination of medications from different drug classes provides beneficial or ameliorative effects in treating otologic conditions (e.g., tinnitus or vertigo) or an otologic symptom (e.g., tinnitus or vertigo) associated with a disease or disorder (e.g., headache or inflammatory intestinal disorder) in a subject in need thereof. For example, retrospective analysis of the preliminary clinical data indicated that an otologic condition or otologic symptom associated with a disease or disorder disclosed herein can be treated with a combined therapy of two or more drugs selected from the following drug classes: tricyclic antidepressants, anti-seizure medications, beta blockers, carbonic anhydrase inhibitors, selective serotonin reuptake inhibitors, selective norepinephrine reuptake inhibitors, calcium or sodium channel blockers, serotonin norepinephrine reuptake inhibitors, specific serotonin antidepressants, tetracyclic and unicyclic antidepressants, tricyclic secondary amines, tricyclic tertiary amines, and antidepressants/serotonin modulators. Examples of tricyclic antidepressants include, but are not limited to, amineptine, amitriptyline, amitriptylinoxide butriptyline, clomipramine, demexiptiline, desipramine, dibenzepin, dimethacrine, dosulepine, doxepin, imipramine, imipraminoxide, iprindole, lofepramine, melitracen, metapramine, nitroxazepine, nortriptyline, noxiptyline, opipramol, pipofezine, propizepine, protriptyline, quinupramine, tianeptine, and trimipramine. Examples of antiseizure medications include, but are not limited to, acetazolamide, carbamazepine, clobazam, clonazepam, diazepam, divalproex sodium, ethosuximide, ethotoin, felbamate, fosphenytoin, gabapentin, lamotrigine, lacosamide, levetiracetam, lorazepam, mephenyloin, metharbital, methsuximide, methazolamide, nitrazepam, oxcarbazepine, phenobarbital, phenytoin, phensuximide, pregabalin, primidone, rufinamide, sodium valproate, stiripentol, tiagabine, topiramate, trimethadione, valproic acid, vigabatrin, and zonisamide. Examples of beta blockers include, but are not limited to, alprenolol, bopindolol, bupranolol, carteolol, cloranolol, mepindolol, nadolol, oxprenolol, penbutolol, pindolol, iodopindolol, propranolol, sotalol, tertatolol, timolol, acebutolol, atenolol, betaxolol, bevantolol, bisoprolol, celiprolol, epanolol, esmolol, landiolol, metoprolol, nebivolol, practolol, S-atenolol, talinolol, butaxamine, arotinolol, carvedilol, and labetalol. Examples of carbonic anhydrase inhibitors include, but are not limited to, acetazolamide, dichlorphenamide, and zonisamide. Examples of selective serotonin reuptake inhibitors, include but are not limited to, citalopram, escitalopram, fluoxetine, fluvoxamine, indalpine, paroxetine, sertraline, and zimelidine. Examples of selective norepinephrine reuptake inhibitors, include but are not limited to, desvenlafaxine, duloxetine, levomilnacipran, milnacipran, tofenacin, and venlafaxine. Examples of calcium or sodium channel blockers, include but are not limited to, ethadione, paramethadione, trimethadione, ethosuximide, mesuximide, phensuximide, gabapentin, pregabalin, imepitoin, lamotrigine, topiramate, verapamil and zonisamide. Examples of tetracyclic and unicyclic antidepressants include, but are not limited to, bupropion, amoxapine, mirtazapine, and maprotiline.

In a further embodiment, the combined therapy disclosed herein to treat an otologic condition or symptom (e.g., tinnitus and vertigo) associated with a disease or disorder (e.g., headache or inflammatory intestinal disorder) comprises a tricyclic antidepressant used in combination with an anti-seizure medication, a calcium or sodium channel blocker, a beta blocker, a carbonic anhydrase inhibitor, a selective serotonin reuptake inhibitor, and/or a selective norepinephrine inhibitor. In yet a further embodiment, the combined therapy disclosed herein to treat and otologic condition or symptom (e.g., tinnitus and vertigo) associated with a disease or disorder (e.g., headache or inflammatory intestinal disorder) comprises an anti-seizure medication used in combination with a calcium or sodium channel blocker, beta blocker, and/or carbonic anhydrase inhibitor. In another embodiment, the combined therapy disclosed herein to treat and otologic condition or symptom (e.g., tinnitus and vertigo) associated with a disease or disorder (e.g., headache or inflammatory intestinal disorder) comprises a selective serotonin reuptake inhibitor used in combination with an anti-seizure medication, calcium or sodium channel blocker, beta blocker, and/or carbonic anhydrase inhibitor. In yet another embodiment, the combined therapy disclosed herein to treat and otologic condition or symptom (e.g., tinnitus and vertigo) associated with a disease or disorder (e.g., headache or inflammatory intestinal disorder) comprises a calcium or sodium channel blocker used in combination with a carbonic anhydrase inhibitor.

The disclosure provides compositions for treating an otologic condition (e.g., tinnitus) or an otologic symptom (e.g., tinnitus and vertigo) associated with a disease or disorder (e.g., headache or inflammatory intestinal disorder). The compositions of the disclosure comprise a first medication and a second medication selected from the following drug classes: tricyclic antidepressants, anti-seizure medications, beta blockers, carbonic anhydrase inhibitors, selective serotonin reuptake inhibitors, selective norepinephrine reuptake inhibitors, calcium or sodium channel blockers, serotonin norepinephrine reuptake inhibitors, specific serotonin antidepressants, unicyclic antidepressants, tricyclic secondary amines, tricyclic tertiary amines, and antidepressants/serotonin modulators, wherein the first medication and the second medication are not from the same drug class. In a further embodiment, the composition of the disclosure comprises a first medication and a second medication in a ratio of 20:1 to 1:20, 19:1 to 1:19, 18:1 to 1:18, 17:1 to 1:17, 16:1 to 1:16, 15:1 to 1:15, 14:1 to 1:14, 13:1 to 1:13, 12:1 to 1:12, 11:1 to 1:11, 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, or 1:1.

The disclosure provides a composition which comprises a first medication of nortriptyline and a second medication selected from an anti-seizure medication, a beta blocker, a calcium or sodium channel blocker, and a carbonic anhydrase inhibitor. In another embodiment, a composition disclosed herein comprises nortriptyline at a dose of about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, or a range that includes or is between any two of the foregoing doses (e.g., from 1 mg to 125 mg of nortriptyline). In another embodiment, a composition of the disclosure comprises a first medication of nortriptyline and a second medication of topiramate. In yet another embodiment, a composition of the disclosure comprises a first medication of nortriptyline and a second medication of gabapentin. In a further embodiment, a composition of the disclosure comprises a first medication of nortriptyline and a second medication of topiramate. In yet a further embodiment, a composition of the disclosure comprises a first medication of nortriptyline and a second medication of propranolol. In another embodiment, a composition of the disclosure comprises a first medication of nortriptyline and a second medication of verapamil. In yet another embodiment, a composition of the disclosure comprises a first medication of nortriptyline and a second medication of acetazolamide.

The disclosure also provides a composition that comprises a first medication of amitriptyline and a second medication selected from an anti-seizure medication, a beta blocker, a calcium or sodium channel blocker, and a carbonic anhydrase inhibitor. In a further embodiment, a composition disclosed herein comprises amitriptyline at a dose of about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, or a range that includes or is between any two of the foregoing doses (e.g., from 1 mg to 125 mg of amitriptyline). In a particular embodiment, a composition of the disclosure comprises a first medication of amitriptyline and a second medication of topiramate. In another embodiment, a composition of the disclosure comprises a first medication of amitriptyline and a second medication of gabapentin. In yet another embodiment, a composition of the disclosure comprises a first medication of amitriptyline and a second medication of propranolol. In a further embodiment, a composition of the disclosure comprises a first medication of amitriptyline and a second medication of verapamil. In yet a further embodiment, a composition of the disclosure comprises a first medication of amitriptyline and a second medication of acetazolamide.

The disclosure further provides a composition that comprises a first medication of propranolol and a second medication selected from a tricyclic antidepressant and a selective serotonin reuptake inhibitor. In yet another embodiment, a composition disclosed herein comprises propranolol at a dose of about 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg or a range that includes or is between any two of the foregoing doses (e.g., from 9 mg to 160 mg of propranolol). In a further embodiment, a composition of the disclosure comprises a first medication of propranolol and a second medication of nortriptyline. In yet a further embodiment, a composition of the disclosure comprises a first medication of propranolol and a second medication of amitriptyline. In another embodiment, a composition of the disclosure comprises a first medication of propranolol and a second medication of paroxetine.

In yet another embodiment, the disclosure provides for a composition that comprises a first medication of topiramate and a second medication selected from a tricyclic antidepressant, a selective serotonin reuptake inhibitor, a calcium or sodium channel blocker. In a certain embodiment, a composition disclosed herein comprises topiramate at a dose of about 7 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, or a range that includes or is between any two of the foregoing doses (e.g., from 7 mg to 200 mg of topiramate). In a further embodiment, a composition of the disclosure comprises a first medication of topiramate and a second medication of nortriptyline. In another embodiment, a composition of the disclosure comprises a first medication of topiramate and a second medication of amitriptyline. In yet another embodiment, a composition of the disclosure comprises a first medication of topiramate and a second medication of paroxetine. In another embodiment, a composition of the disclosure comprises a first medication of topiramate and a second medication of verapamil.

The disclosure also provides a composition that comprises a first medication of gabapentin and a second medication selected from a tricyclic antidepressant, a selective serotonin reuptake inhibitor, a calcium or sodium channel blocker. In a certain embodiment, a composition disclosed herein comprises gabapentin at a dose of about 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, or a range that includes or is between any two of the foregoing doses (e.g., from 40 mg to 2700 mg of gabapentin). In a further embodiment, a composition of the disclosure comprises a first medication of gabapentin and a second medication of nortriptyline. In another embodiment, a composition of the disclosure comprises a first medication of gabapentin and a second medication of amitriptyline. In yet another embodiment, a composition of the disclosure comprises a first medication of gabapentin and a second medication of paroxetine. In another embodiment, a composition of the disclosure comprises a first medication of gabapentin and a second medication of verapamil.

The disclosure provides a composition that comprises a first medication of verapamil and a second medication selected from a tricyclic antidepressant, a selective serotonin reuptake inhibitor, a calcium or sodium channel blocker, and a carbonic anhydrase inhibitor. In a certain embodiment, a composition disclosed herein comprises verapamil at a dose of about 20 mg, 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, or a range that includes or is between any two of the foregoing doses (e.g., from 20 mg to 2700 mg of verapamil). In a further embodiment, a composition of the disclosure comprises a first medication of verapamil and a second medication of nortriptyline. In another embodiment, a composition of the disclosure comprises a first medication of verapamil and a second medication of amitriptyline. In yet another embodiment, a composition of the disclosure comprises a first medication of verapamil and a second medication of paroxetine. In a further embodiment, a composition of the disclosure comprises a first medication of verapamil and a second medication of topiramate. In another embodiment, a composition of the disclosure comprises a first medication of verapamil and a second medication of gabapentin. In yet another embodiment, a composition of the disclosure comprises a first medication of verapamil and a second medication of acetazolamide.

The disclosure provides a composition that comprises a first medication of acetazolamide and a second medication selected from a tricyclic antidepressant, and a calcium or sodium channel blocker. In a certain embodiment, a composition disclosed herein comprises acetazolamide at a dose of about 60 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg, 1250 mg, 1300 mg, 1350 mg, 1400 mg, 1450 mg, 1500 mg, or a range that includes or is between any two of the foregoing doses (e.g., from 60 mg to 1500 mg of acetazolamide). In another embodiment, a composition of the disclosure comprises a first medication of acetazolamide and a second medication of nortriptyline. In yet another embodiment, a composition of the disclosure comprises a first medication of acetazolamide and a second medication of amitriptyline. In a certain embodiment, a composition of the disclosure comprises a first medication of acetazolamide and a second medication of paroxetine.

The disclosure provides a composition that comprises a first medication of paroxetine and a second medication selected from an antiseizure medication, a calcium or sodium channel blocker, a beta blocker, and a carbonic anhydrase inhibitor. In a certain embodiment, a composition disclosed herein comprises paroxetine at a dose of about 3 mg, 5 mg, 10 mg, 12 mg, 14 mg, 15 mg, 16 mg, 18 mg, 20 mg, 22 mg, 24 mg, 25 mg, 26 mg, 28 mg, 30 mg, 32 mg, 34 mg, 35 mg, 36 mg, 38 mg, 40 mg, or a range that includes or is between any two of the foregoing doses (e.g., from 3 mg to 40 mg of paroxetine). In another embodiment, a composition of the disclosure comprises a first medication of paroxetine and a second medication of topiramate. In yet another embodiment, a composition of the disclosure comprises a first medication of paroxetine and a second medication of gabapentin. In a certain embodiment, a composition of the disclosure comprises a first medication of paroxetine and a second medication of verapamil. In a certain embodiment, a composition of the disclosure comprises a first medication of paroxetine and a second medication of acetazolamide.

It is further expected that a composition of the disclosure could be further combined with a dietary supplement in treating said ontological conditions or otologic symptom associated with a disease or disorder in a subject in need thereof. Examples of dietary supplements, include but are not limited to, vitamin supplements (e.g., vitamin $B_2$), mineral supplements (e.g., magnesium), specialty supplements (e.g., melatonin, glucosamine, fish oil, etc.) or a botanical or herbal supplement (e.g., feverfew).

The disclosure further provides that a composition disclosed herein is formulated as a pharmaceutical composition in a single unit dosage form, or a multi-unit dosage form. Such pharmaceutical compositions may comprise physiologically acceptable surface-active agents, carriers, diluents, excipients, smoothing agents, suspension agents, film forming substances, and coating assistants, or combinations thereof. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methyl acetate-methacrylate copolymer as a derivative of polyvinyl may be used as suspension agents; and plasticizers such as ester phthalates and the like may be used as suspension agents.

The term "carrier" defines a chemical compound that facilitates the incorporation of medications disclosed herein into cells or tissues. For example, dimethyl sulfoxide (DMSO) is a commonly utilized carrier as it facilitates the uptake of many organic compounds into the cells or tissues of an organism.

The term "diluent" defines a chemical compound that will dissolve the medications of interest as well as stabilize the biologically active form of the medication. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a medication.

The term "physiologically acceptable" defines a carrier or diluent that does not abrogate the biological activity and properties of the medications disclosed herein.

Techniques for formulation and administration of the compositions described herein may be found in "Remington's Pharmaceutical Sciences," Mack Publishing Co., Easton, Pa., 18th edition, 1990.

Suitable routes of administration of the pharmaceutical composition may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The pharmaceutical composition can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein thus may be formulated in conventional manner using one or more physiologically acceptable carriers comprising excipients and auxiliaries which facilitate processing of the active medications into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active medications in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the medications may be in powder form for constitution with a suitable vehicle, e.g., sterile pyrogen-free water, before use.

For oral administration, the medications can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the medications may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the pharmaceutical compositions may take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insulator may be formulated containing a powder mix of the medications and a suitable powder base such as lactose or starch.

Further disclosed herein are various pharmaceutical compositions well known in the pharmaceutical art for uses that include intraocular, intranasal, and intra-auricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Opthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocil. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intra-auricular delivery include suspensions and ointments for topical application in the ear. Common solvents for such aural formulations include glycerin and water.

The pharmaceutical composition may also be formulated in rectal compositions such as suppositories or retention enemas, e.g., containing conventional suppository bases such as cocoa butter or other glycerides.

In addition to the pharmaceutical formulations described previously, the medications may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethyl sulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

The disclosure provides for methods of treatment of an otologic condition or an otologic symptom associated with a disease or disorder in a subject in need thereof, comprising: administering a therapeutically effective amount of a composition or combined therapy disclosed herein. Examples of an otologic conditions and otologic symptom include, but are not limited to, tinnitus, fluctuating or sudden hearing loss, sensorineural hearing loss, dizziness, and vertigo. Examples of disease or disorders that give rise to otologic symptoms, include but are not limited to, neck pain, headache, irritable bowel syndrome, interstitial cystitis, migraine-related disorders, and fibromyalgia. In a certain embodiment, the disclosure provides for use of a composition or combined therapy disclosed herein for the treatment of tinnitus in a subject in need thereof. In another embodiment, the disclosure provides for use of a composition or combined therapy disclosed herein for the treatment of vertigo in a subject in need thereof. In yet another embodiment, the disclosure provides for use of a composition or combined therapy disclosed herein for the treatment of fluctuating or sudden hearing loss in a subject in need thereof. In another embodiment, the disclosure provides for use of a composition or combined therapy disclosed herein for the treatment of dizziness in a subject in need thereof. In yet another embodiment, the disclosure provides for use of a composition or combined therapy disclosed herein for the treatment of sensorineural hearing loss in a subject in need thereof.

In some embodiments, one of the advantages of the compositions and combined therapies disclosed herein is that medications can be co-administered at a sub-maximal dose levels and still achieve an efficacious result. In doing so, use of the compositions composition and combined therapies described herein can avoid side-effects seen when the medications are administered alone at a maximal dose. In various embodiments, the side effects are selected from the group consisting of stroke, tremors, sedation, gastrointestinal problems, neurological problems, increased risk of death, cerebrovascular events, movement disorder, dystonia, akathisia, Parkinson's movement disorder, tardive dyskinesia, cognitive disorders, prolactinoma, catalepsy, psychosis, neuroleptic malignant syndrome, heart problems, pulmonary problems, diabetes, liver failure, suicidality, sedation, orthostatic hypotension, choking, dizziness, tachycardia, blood abnormalities (including abnormal triglyceride levels, increased cholesterol levels, dyslipidemia, and hyperglycemia), syncope, seizures, dysphagia, priapism, thrombotic thrombocytopenic purpura, disruption of body temperature regulation, insomnia, agitation, anxiety, somnolence, aggressive reaction, headache, constipation, nausea, dyspepsia, vomiting, abdominal pain, saliva increase, toothache, rhinitis, coughing, sinusitis, pharyngitis, dyspnea, back pain, chest pain, fever, rash, dry skin, seborrhea, increased upper respiratory infection, abnormal vision, arthralgia, hypoesthesia, manic reaction, concentration impairment, dry mouth, pain, fatigue, acne, pruritus, myalgia, skeletal pain, hypertension, diarrhea, confusion, asthenia, urinary incontinence, sleepiness, increased duration of sleep, accommodation disturbance, palpitations, erectile dysfunction, ejaculatory dysfunction, orgasmic dysfunction, lassitude, increased pigmentation, increased appetite, automatism, increased dream activity, diminished sexual desire, nervousness, depression, apathy, catatonic reaction, euphoria, increased libido, amnesia, emotional liability, nightmares, delirium, yawning, dysarthria, vertigo, stupor, paranesthesia, aphasia, hypoesthesia, tongue paralysis, leg cramps, torticollis, hypotonia, coma, migraine, hyperreflexia, choreoathetosis, anorexia, flatulence, stomatitis, melena, hemorrhoids, gastritis, fecal incontinence, eructation, gastroesophageal reflux, gastroenteritis, esophagitis, tongue discoloration, cholelithiasis, tongue edema, diverticulitis, gingivitis, discolored feces, gastrointestinal hemorrhage, hematemesis, edema, rigors, malaise, pallor, enlarged abdomen, ascites, sarcoidosis, flushing, hyperventilation, bronchospasm, pneumonia, stridor, asthma, increased sputum, aspiration, photosensitivity, increased sweating, acne, decreased sweating, alopecia, hyperkeratosis, skin exfoliation, bullous eruption, skin ulceration, aggravated psoriasis, furunculosis, verruca, dermatitis lichenoid, hypertrichosis, genital pruritus, urticaria, ventricular tachycardia, angina pectoris, premature atrial contractions, T wave inversion, ventricular extrasystoles, ST depression, AV block, myocarditis, abnormal accommodation, xerophthalmia, diplopia, eye pain, blepharitis, photopsia, photophobia, abnormal lacrimation, hyponatremia, creatine phosphokinase increase, thirst, weight decrease, decreased serum iron, cachexia, dehydration, hypokalemia, hypoproteinemia, hyperphosphatemia, hypertriglyceridemia, hyperuricemia, hypoglycemia, polyuria, polydipsia, hematuria, dysuria, urinary retention, cystitis, renal insufficiency, arthrosis, synostosis, bursitis, arthritis, menorrhagia, dry vagina, nonpuerperal lactation, amenorrhea, female breast pain, leucorrhea, mastitis, dysmenorrhea, female perineal pain, intermenstrual bleeding, vaginal hemorrhage, increased SGOT, increased SGPT, cholestatic hepatitis, cholecystitis, hepatitis, hepatocellular damage, epistaxis, superficial phlebitis, thrombophlebitis, thrombocytopenia, tinnitus, hyperacusis, decreased hearing, anemia, hypochromic anemia, normocytic anemia, granulocytopenia, leukocytosis, lymphadenopathy, leucopenia, Pelger-Huet anomaly, gynecomastia, male breast pain, antidiuretic hormone disorder, bitter taste, micturition disturbances, oculogyric crisis, abnormal gait, involuntary muscle contraction, and increased injury.

In some embodiments, one or more of the medications of a composition or combined therapy disclosed herein is administered at a sub-maximal dosage level. In various such embodiments, the dosage of one or more of the medications of the composition or combination therapy disclosed herein is less than about 75%, 60%, 50%, 40%, 30%, 20%, or 10% of the maximal dose. By "maximal dose," it is meant the minimum dose where further increases in the dose do not result in any significant increase in therapeutic effect when administering the agent alone. In some embodiments, one or more of the medications of the composition or combination therapy disclosed herein is administered at a dose that is less than an efficacious dose for the medications when they are administered alone. In various embodiments, the dosage is less than about 75%, 60%, 50%, 40%, 30%, 20%, or 10% of an efficacious dose. By "efficacious dose," it is meant the minimal dosage that is required to achieve a clinically relevant therapeutic effect when administering the agent alone.

In some embodiments, administration of a composition or combined therapy disclosed herein results in a rapid onset of an efficacious effect. In other words, in some embodiments, efficacious activity is achieved faster than when the medications are used in combination than when they are singly administered. In various embodiments, the rapid onset of efficacious activity is demonstrated by a clinically relevant therapeutic effect being achieved greater than about 30%, 40%, 50%, 60%, 70%, 80%, 90%, 100%, 110%, 130%, 150%, 200%, 300%, 400%, or 500% faster than when the medications are administered alone at an efficacious dose. In some embodiments, the rapid onset of efficacious activity is demonstrated by a greater percentage of patients experiencing an efficacious effect after a specified period of time of the combined therapy when compared to administration of the medications singly at an efficacious dose. In various embodiments, the percentage of patients experiencing an efficacious effect from the combined therapy is increased by greater than about 20%, 30%, 40%, 50%, 60%, 70%, 80%, 90%, 100%, 110%, 130%, 150%, 200%, 300%, 400%, or 500% in comparison to administration of each mediation alone at an efficacious dose. In some embodiments, the specified period of time is from 1 to 8 weeks.

In a certain embodiment, the disclosure also provides that administration of an efficacious dose of a composition disclosed or combined therapy disclosed herein to a subject with tinnitus which results in an improvement in the subject's tinnitus functional index, a decrease in the tinnitus loudness level in the subject, and/or a decrease in the number of days in which subject suffers from annoying tinnitus.

The following examples are intended to illustrate but not limit the disclosure. While they are typical of those that might be used, other procedures known to those skilled in the art may alternatively be used.

EXAMPLES

Subjects and recruitment method. Adult subjects are recruited via a high-volume tertiary referral center. Subjects will be enrolled in the studies: if the subject (1) has moderate to severe (subjective severity) symptoms; (2) compliant with their mediations; (3) can attend study visits. After obtaining an informed consent, the test subjects will undergo a comprehensive medical history review and be physically examined. Any previous examination tests, if applicable, will be obtained and evaluated pre-trial. Exclusion criteria will then be applied. Such exclusion criteria can include pregnancy, psychosis, definite Meniere's disease, neurological neoplasm, active external or middle ear disease, history of endolymphatic sac surgery, history of allergic reaction to or adverse events with the study medications, suffering from a medical condition or having a history that may be concerning to the investigators' clinical opinion, and contraindications for the medications which prevent subjects from randomization.

General Study design. A randomized, double-blinded, placebo controlled, single institutional 12-week trial will be performed. Subjects will be randomly assigned to the experimental or control groups using a block randomization technique. Both groups will receive instructions for dietary and lifestyle modifications to control for any potential confounding effects due to symptom triggers. The experimental group will receive the proposed combined medication regimen according to an algorithm with escalating doses as validated in preliminary retrospective studies. Escalating doses will continue until symptom improvement or until a maxim dose has been reached. If the subjects do not improve at the maximum dosage level; they will be considered to have failed medication therapy and will be tapered down to zero with gradual dose de-escalation. The subjects will visit a second time at week 8.

Subjects in the control group will receive a placebo that will be supplied in a similar size and shape to the experimental drugs. These subjects will also follow similar escalation protocol. The pills will be supplied from the pharmacy with a unique identifier and the subjects' group will not be disclosed to the team prior to the end of the study. All subjects will be asked to report potential side effects. Those reporting potential side effects will be seen and examined by medical practitioners to assess the safety of their continued enrollment and/or need for additional treatment.

General Study evaluations. Following enrolment in the study, subjects will be followed over a course of 8 weeks. Subjects will be seen twice, one pre-trial visit and one at the end of the $8^{th}$ week. Data regarding independent variables such as demographics, medical history, medications, imaging studies, and previous treatments will be collected during the pre-trial visit. Primary outcomes will be evaluated. These measures will help determine adjustment of medication dosages. Subjects will additionally be asked to fill in surveys about their conditions and their symptoms at the pre-trial visit as well as post-trial ($8^{th}$ week) visit. Accomplishment of the study aims will provide a pilot assessment of the effectiveness of combined therapy in the treatment of condition and the medication's side effect profile.

Study design for the combined treatment of Tinnitus with an anticonvulsant and an antidepressant. A randomized, double-blinded, placebo controlled, single institutional 12-week study will be carried out. Subjects will be randomly assigned to the experimental or control groups using a block randomization technique. Both groups will receive instructions for tinnitus dietary and lifestyle modifications to control for any potential confounding effects from tinnitus triggers. The experimental group will receive the proposed migraine medication regimen according to an algorithm with escalating doses that has been developed and validated in preliminary retrospective studies. The algorithm for the experimental group is as follows: subjects in the experimental group will be started on a pill qhs (every bedtime) containing 7.5 mg nortriptyline plus 10 mg topiramate. They will receive a phone call every week to gauge their response to the study drug (or placebo) based on a visual analogue scale. On this weekly basis call, subjects will be instructed to increase the dosage of medications (7.5 mg-step for nortriptyline plus 10 mg-step for topiramate) if tinnitus symptoms do not improve. This process will continue until they reach a maximum dose of 60 mg for nortriptyline and 80 mg for topiramate. If they do not improve at this dosage level; they will be considered to have failed medication therapy and will be tapered down to zero with gradual dose de-escalation. Subjects will be instructed to avoid increasing their medication dosage if their symptoms have improved. The subjects will visit a second time at week 8.

Subjects in the control group will receive a placebo (Microcrystalline Cellulose; PH105) that will be supplied in a similar size and shape to the experimental drug. These subjects will also follow similar escalation protocol as the PI and Co-PI will be blinded to the randomization. The pills will be supplied from the pharmacy with a unique identifier and the subjects' group will not be disclosed to the team prior to the end of the study. The different dosage combinations are made by the pharmacist in a single custom-made pill for the subjects' conveniences. All subjects will be asked to report potential side effects. Those reporting potential side effects will be seen and examined by the Co-PI to assess the safety of their continued enrollment and/or need for additional treatment.

Study evaluations for Tinnitus. Following enrolment in the study, subjects will be followed over a course of 8 weeks. Subjects will be seen twice, one pre-trial visit and one at the end of the $8^{th}$ week. Data regarding independent variables such as demographics, medical history, medications, vestibular migraine related symptoms and clinical features, audiograms, imaging studies, and previous treatments will be collected during the pre-trial visit. Primary outcomes will include the percentage of waking hours the subject is aware of the tinnitus, minimum masking level (MML) and tinnitus loudness based on a visual analogue scale. Subjects' will additionally be asked to fill in surveys about pre- and post-participation scores on Tinnitus Functional Inventory (TFI), Perceived Stress Scale (PSS), and Short Form 12. The scores will be compared to evaluate for potential changes in the subject's condition. Secondary treatment outcomes for tinnitus will include changes in the tinnitus handicap. These measures provide a pilot assessment of the effectiveness of nortriptyline-topiramate combination in the treatment of tinnitus and their side effect profile.

Tricyclic antidepressant and anti-seizure combination. Nortriptyline combined with topiramate: 13 patients were treated with the combination starting at a dose of 1 mg of nortriptyline and 7 mg of topiramate. The dosages were gradually escalated up to 125 mg of nortriptyline and 200 mg of topiramate. Of the 13 patients treated, 9 had a substantial improvement in their tinnitus functional index and annoyance. The tinnitus loudness level decreased as well. The patients with aural pressure/pain, fluctuating hearing loss, dizziness/vertigo, neck stiffness/headache, irritable bowel syndrome/interstitial cystitis, or fibromyalgia experienced an improvement in their symptoms.

Nortriptyline combined with gabapentin: 5 patients treated with this combination starting at a dose of 1 mg of nortriptyline and 40 mg of gabapentin. The dosages were gradually escalated up to 125 mg of nortriptyline and 2700 mg of gabapentin daily. Of the 5 patients treated, 3 had a substantial improvement in their tinnitus functional index and annoyance. The tinnitus loudness level decreased as well.

Amitriptyline combined with topiramate: 4 patients were treated with the combination starting at a dose of 1 mg of amitriptyline and 7 mg of topiramate. The dosages were gradually escalated up to 125 mg of nortriptyline and 200 mg of topiramate. Of the 4 patients treated, 3 had a substantial improvement in their tinnitus functional index and annoyance averaged over the previous week prior to presentation. The tinnitus loudness level decreased as well.

Amitriptyline combined with gabapentin: 5 patients treated with this combination starting at a dose of 1 mg of amitriptyline and 40 mg of gabapentin. The dosages were gradually escalated up to 125 mg of amitriptyline and 2700 mg of gabapentin daily. Of the 5 patients treated, 4 had a substantial improvement in their tinnitus functional index and annoyance. The tinnitus loudness level decreased as well. Average number of days with annoying tinnitus decreased.

Tricyclic antidepressant and beta blocker combination. Nortriptyline combined with propranolol: 3 patients treated with this combination starting at a dose of 1 mg of nortriptyline and 9 mg of propranolol. The dosages were gradually escalated up to 125 mg of nortriptyline and 160 mg of propranolol daily. Of the 3 patients treated, 2 had a substantial improvement in their tinnitus functional index. Average number of days with very annoying tinnitus decreased.

Amitriptyline combined with propranolol: 3 patients treated with this combination starting at a dose of 1 mg of amitriptyline and 9 mg of propranolol. The dosages were gradually escalated up to 125 mg of amitriptyline and 160 mg of propranolol daily. Of the 3 patients treated, 2 had a substantial improvement in their tinnitus functional index.

Tricyclic antidepressant and calcium channel blocker combination. Nortriptyline combined with verapamil: 12 patients treated with this combination starting at a dose of 1 mg of nortriptyline and 20 mg of verapamil. The dosages were gradually escalated up to 125 mg of nortriptyline and 360 mg of verapamil daily. Of the 12 patients treated, 9 had a substantial improvement in their tinnitus functional index.

Amitriptyline combined with verapamil: 3 patients treated with this combination starting at a dose of 1 mg of amitriptyline and 20 mg of verapamil. The dosages were gradually escalated up to 125 mg of amitriptyline and 360 mg of verapamil daily. Of the 3 patients treated, 2 had a substantial improvement in their tinnitus functional index.

Tricyclic antidepressant and carbonic anhydrase inhibitor combination. Nortriptyline combined with acetazolamide: 5 patients treated with this combination starting at a dose of 1 mg of nortriptyline and ~60 mg of acetazolamide. The dosages were gradually escalated up to 125 mg of nortriptyline and 1500 mg of acetazolamide daily. Of the 5 patients treated, 3 had a substantial improvement in their tinnitus functional index.

Amitriptyline combined with acetazolamide: 3 patients treated with this combination starting at a dose of 1 mg of amitriptyline and ~60 mg of acetazolamide. The dosages were gradually escalated up to 125 mg of amitriptyline and 1500 mg of acetazolamide daily. Of the 3 patients treated, 2 had a substantial improvement in their tinnitus functional index.

Selective serotonin reuptake inhibitor and anti-seizure combination. Paroxetine combined with topiramate: 8 patients were treated with the combination starting at a dose of 3 mg of paroxetine and 7 mg of topiramate. The dosages were gradually escalated up to 40 mg of paroxetine and 200 mg of topiramate. Of the 8 patients treated, 6 had a substantial improvement in their tinnitus functional index and annoyance. The tinnitus loudness level decreased as well. The patients with aural pressure/pain, fluctuating hearing loss, dizziness/vertigo, neck stiffness/headache, irritable bowel syndrome/interstitial cystitis, or fibromyalgia experienced an improvement in their symptoms.

Paroxetine combined with gabapentin: 4 patients treated with this combination starting at a dose of 3 mg of paroxetine and 40 mg of gabapentin. The dosages were gradually escalated up to 40 mg of paroxetine and 2700 mg of gabapentin daily. Of the 4 patients treated, 2 had a substantial improvement in their tinnitus functional index, loudness, and annoyance.

Selective serotonin reuptake inhibitor and beta blocker combination. Paroxetine combined with propranolol: 4 patients treated with this combination starting at a dose of 3 mg of paroxetine and 9 mg of propranolol. The dosages were gradually escalated up to 40 mg of paroxetine and 160 mg of propranolol daily. Of the 4 patients treated, 3 had a substantial improvement in their tinnitus functional index. Average number of days with very annoying tinnitus decreased.

Selective serotonin reuptake inhibitor and calcium channel blocker combination. Paroxetine combined with verapamil: 7 patients treated with this combination starting at a dose of 3 mg of paroxetine and 20 mg of verapamil. The dosages were gradually escalated up to 40 mg of paroxetine and 360 mg of verapamil daily. Of the 7 patients treated, 5 had a substantial improvement in their tinnitus functional index. The patients with aural pressure/pain, fluctuating hearing loss, dizziness/vertigo, neck stiffness/headache, irritable bowel syndrome/interstitial cystitis, or fibromyalgia experienced an improvement in their symptoms.

Selective serotonin reuptake inhibitor and carbonic anhydrase inhibitor combination. Paroxetine combined with acetazolamide: 4 patients treated with this combination starting at a dose of 3 mg of paroxetine and ~60 mg of acetazolamide. The dosages were gradually escalated up to 40 mg of paroxetine and 1500 mg of acetazolamide daily. Of the 4 patients treated, 2 had a substantial improvement in their tinnitus functional index.

Anti-seizure and calcium channel blocker combination. Verapamil combined with topiramate: 5 patients were treated with the combination starting at a dose of 20 mg of verapamil and 7 mg of topiramate. The dosages were gradually escalated up to 360 mg of verapamil and 200 mg of topiramate. Of the 4 patients treated, 2 had a substantial improvement in their tinnitus functional index and annoyance averaged over the previous week prior to presentation. The tinnitus loudness level decreased as well.

Verapamil combined with gabapentin: 6 patients treated with this combination starting at a dose of 20 mg of verapamil and 40 mg of gabapentin. The dosages were gradually escalated up to 360 mg of verapamil and 2700 mg of gabapentin daily. Of the 6 patients treated, 4 had a substantial improvement in their tinnitus functional index and annoyance. The tinnitus loudness level decreased as well. Average number of days with annoying tinnitus decreased.

Calcium channel blocker and carbonic anhydrase inhibitor combination. Verapamil combined with acetazolamide: 4 patients treated with this combination starting at a dose of 20 mg of verapamil and 60 mg of acetazolamide. The dosages were gradually escalated up to 360 mg of verapamil and 1500 mg of acetazolamide daily. Of the 4 patients treated, 3 had a substantial improvement in their tinnitus functional index.

It will be understood that various modifications may be made without departing from the spirit and scope of this disclosure. Accordingly, other embodiments are within the scope of the following claims.

What is claimed is:

1. A method of treating tinnitus in a human subject in need thereof, comprising: orally administering to the subject a combined therapy comprising therapeutically effective amounts of nortriptyline and topiramate, wherein the combined therapy comprises from 7.5 mg to 75 mg of nortriptyline and from 10 mg to 100 mg of topiramate, and wherein the combined therapy has synergistic effect in treating tinnitus.

2. The method of claim 1, wherein administration of the combined therapy to the subject provides one or more of the following effects:
   improvement in a subject's tinnitus functional index;
   a decrease in the average number days in which the subject has annoying tinnitus; and/or
   a decrease in the level of tinnitus loudness.

3. The method of claim 1, wherein nortriptyline and topiramate are concomitantly administered.

4. The method of claim 1, wherein nortriptyline and topiramate are sequentially administered.

5. The method of claim 1, wherein the combined therapy comprises a pharmaceutical composition which contains from 7.5 mg to 60 mg of nortriptyline and from 10 mg to 80 mg of topiramate.

6. The method of claim 5, wherein the pharmaceutical composition comprises a weight ratio of nortriptyline to topiramate of 7.5:10.

7. The method of claim 5, wherein the pharmaceutical composition is in the form of a pill, a tablet, or a capsule.

8. The method of claim 1, wherein the combined therapy comprises a weight ratio of nortriptyline to topiramate of 7.5:10.

9. The method of claim 1, wherein the subject is administered one or more escalating doses of the combined therapy until there is improvement in the subject's tinnitus, and wherein the lowest dose of the combined therapy comprises 7.5 mg of nortriptyline and 10 mg of topiramate.

10. The method of claim 9, wherein each escalating dose of the combined therapy comprises 7.5 mg of nortriptyline and 10 mg of topiramate, and wherein the dose is escalated on a weekly basis.

* * * * *